United States Patent [19]

Schorlemmer et al.

[11] Patent Number: 4,963,577

[45] Date of Patent: Oct. 16, 1990

[54] USE OF THE THIAZOLE DERIVATIVE TIPROTIMOD FOR THE PREPARATION OF AN AGENT FOR THE THERAPY OF VIRUS INFECTIONS

[75] Inventors: Hans U. Schorlemmer; Hans H. Sedlacek; Joachim Hilfenhaus, all of Marburg, Fed. Rep. of Germany

[73] Assignee: Behringwerke Aktiengesellschaft, Marburg/Lahn, Fed. Rep. of Germany

[21] Appl. No.: 350,957

[22] Filed: May 12, 1989

[30] Foreign Application Priority Data

May 16, 1988 [DE] Fed. Rep. of Germany ....... 3816603

[51] Int. Cl.$^5$ .......................................... A61K 31/425
[52] U.S. Cl. .................................................... 514/369
[58] Field of Search ........................................ 514/369

[56] References Cited

U.S. PATENT DOCUMENTS 4,762,848 8/1988 Scheunemann et al. ............ 514/369

Primary Examiner—Jerome D. Goldberg
Attorney, Agent, or Firm—Finnegan, Henderson, Farabow, Garrett & Dunner

[57] ABSTRACT

The use of the thiazole derivative tiprotimod for the preparation of a pharmaceutical for the therapy of virus infections is described.

4 Claims, No Drawings

USE OF THE THIAZOLE DERIVATIVE TIPROTIMOD FOR THE PREPARATION OF AN AGENT FOR THE THERAPY OF VIRUS INFECTIONS

The invention relates to the use of the thiazole derivative tiprotimod for the preparation of a pharmaceutical to counter virus infections in humans and animals.

Processes for the preparation of tiprotimod and the immunomodulatory effect thereof are described in German Offenlegungsschrift DE 3,508,665 Al, and the structure

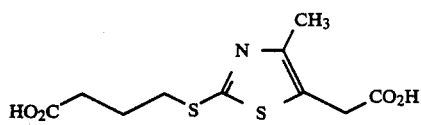

and the name 2-(3-carboxy-1-propylthio)-4-methyl-1,3-thiazol-5-ylacetic acid given for tiprotimod.

Immunological investigations have revealed that there are connections between the decrease in the immunological activity occurring naturally or provoked by external factors and the increase in the risk of infections or tumors. Functional cooperation between all components of the immune system, of humoral and cellular immunity, is of great importance for the defense mechanisms of the living organism and thus for the elimination of foreign bodies and pathogens, mainly microorganisms or neoplastic cells.

It has now been found, surprisingly, that the substance tiprotimod has besides its action as immunostimulator in warm-blooded mammals at a dose which is optimally between 0.5 and 10 mg/kg of body weight, and which is administered parenterally one or more times, a therapeutic effect on viral infectious diseases without at the same time showing toxic side effects. Hence tiprotimod is suitable for the treatment of such diseases. It is possible in animal experiments, for example, to influence a herpes simplex infection which has a fatal course in mice by therapeutic administration of tiprotimod so beneficially that a survival rate of 40% results at the end of the observation period (25 days). No animal in the control group survives in the same observation period.

Accordingly, the invention relates to the use of tiprotimod for the preparation of a pharmaceutical for the therapy of viral infectious diseases, preferably of those caused by herpes simplex or EMC (encephalomyocarditis) viruses as claimed in the patent claims.

The effective therapeutic amount is preferably, but not exclusively, in the range 0.5–10 mg/kg of body weight on parenteral administration.

The active substance can be administered alone or else combined with other pharmaceuticals which have beneficial effects on infections. The active substance can, according to the invention, be administered both parenterally and orally. Suitable for parenteral, specifically intravenous, administration are solutions or suspensions of the active substance in a known pharmaceutically tolerated vehicle.

To prepare aqueous solutions, the active substance is preferably employed in the form of physiologically tolerated salts which are soluble in water. The formulations can contain the customary auxiliaries and excipients. Examples of these are fillers, emulsifiers, lubricants and buffer substances and flavor-correcting agents.

The compound used according to the invention exhibits in the concentration ranges in which it is effective no toxicity and does not lead to local granuloma formation.

The action of the substance is illustrated hereinafter by way of example in standard test methods. The various test models employed are known to be particularly well suited for assessing the quality of the actions of therapeutics against virus infections in humans and animals.

EXAMPLE 1

Therapeutic Infection

For the therapeutic treatment of a herpes simplex HSV-1 virus infection, nude mice (10/group) were infected intradermally with 0.1 ml of virus suspension (strain "Wal"; 1000 $LD_{50}$) per mouse on day 0. The tes substance was administered to the animals intraperitoneally either once or in two doses on consecutive days in concentrations of 0.8, 2.4 and 7.2 mg/kg of body weight (see Table 1). The animals were checked for survival each day for a period of 25 days, and the survival rate was determined. As is evident from Table 2, all the animals in the untreated control group die. Two injections of the test substance (7.2 mg/kg) on days 1 and 2 after infection results in protection (40%) from the virus infection. The test substance distinctly reduces the mortality rate (40%) even with a single dose on day 2 after the infection, and thus has a therapeutic effect on the disease.

EXAMPLE 2

Effect on EMC virus myocarditis in the NMRI mouse

In this case, NMRI mice were initially, at an age of 6 weeks, infected intraperitoneally with the cardiotropic EMC virus (5.5 PFU=plaque-forming units) and then treated in the acute phase of the disease, from the 1st day after the infection, with 1 mg/kg intraperitoneally every 2nd day up to day 10. In order to investigate the effect on the early phase of the viral heart disease, the lethality, weight change, hemodynamics and histological parameters of the mycocarditis in the mice were recorded. It is evident from the available results that administration of tiprotimod (1 mg/kg i.p. every 2nd day) results in an improvement in histological parameters in mice 10 days after an EMC virus infection. The effects on the lethality, hemodynamic parameters and the beneficial effect on the signs of paralysis in the acute phase of the disease are consistent with this.

Thus, in in vivo test models which can be employed to assess therapeutics having antiviral activity, tiprotimod is able to increase markedly the survival rate of the infected animals and to alleviate the symptoms. Tiprotimod can thus be used as a therapeutic for virus infections.

TABLE 1

Treatment of an HSV1 infection in nude mice with tiprotimod - outline of treatment

| Group | Day −1<br>Tiprotimod<br>0.8, 2.4, 7.2 mg/kg<br>1 × i.p. | Day 0<br>HSV1 infection(id)<br>0.1 ml/mouse<br>33 902 1:20 | Day 1<br>Tiprotimod<br>0.8, 2.4, 7.2 mg/kg<br>1 × i.p. | Day 2<br>Tiprotimod<br>0.8, 2.4, 7.2 mg/kg<br>1 × i.p. | Day 25 |
|---|---|---|---|---|---|
| 1. | | | | | |
| 2. | ↓ | ↓ | | | |
| 3. | | ↓ | ↓ | ↓ | |
| 4. | | ↓ | | ↓ | |

Observation period spans Day 0 to Day 25.

TABLE 2

Treatment of an HSV-1 infection in nude mice with tiprotimod - results

| | | Prophylaxis/therapy with tiprotimod Surviving animals | | | |
|---|---|---|---|---|---|
| Group | HSV-1 infection | 0 | 0.8 | 2.4 | 7.2 mg/kg |
| 1 | + | 0/10 | | | |
| 2 | + | | 0/10 | 1/10 | 1/10 |
| 3 | + | | 3/10 | 2/10 | 4/10 |
| 4 | + | | 1/10 | 3/10 | 4/10 |

TABLE 3

Therapeutic effect on virally (EMC virus) induced myocarditis in NMRI mice in the acute phase up to the 10th day of the disease

| Measured parameters | untreated EMC-infected control group | Therapy group 1 mg/kg tiprotimod/ i.p. every 2nd day |
|---|---|---|
| Weight: | | |
| 1st day | 24.9 ± 2.4 g | 26.1 ± 1.8 g |
| 10th day | 27.7 ± 6.5 g | 32.0 ± 3.4 g |
| systolic pressure in the left ventricle of the heart: | 60.0 ± 9.0 mm Hg | 81.0 ± 15.0 mm Hg |
| Histology of the heart: | | |
| Lymphocytic infiltrate: | 11/14 (78.6%) | 2/20 (10%) |
| Fibrosis: | 0 | 0 |
| Focal necroses: | 10/14 (71.4%) | 3/20 (15%) |
| Calcification: | 2/14 (14.3%) | 0 |
| Paralysis: | 8 animals | 0 |
| Deaths | 6 animals | 0 |

We claim:

1. A method for the therapy of viral infectious diseases consisting essentially of administering to a host in need of such therapy an effective amount of the compound 2-(3-carboxy-1-propylthio)-4-methyl-1,3-thoazol-5-ylacetic acid or a physiologically tolerated salt thereof.

2. The method as claimed in claim 1, wherein the virus is herpes simplex or EMC virus.

3. The method as claimed in claim 1 wherein the compound is administered in an amount of 0.1–100 mg/kg of body weight.

4. The method as claimed in claim 1 wherein the compound is administered in an amount of 0.5–10 mg/kg of body weight.

* * * * *